(12) United States Patent
Baril et al.

(10) Patent No.: US 10,945,734 B2
(45) Date of Patent: Mar. 16, 2021

(54) ROTATION KNOB ASSEMBLIES AND SURGICAL INSTRUMENTS INCLUDING THE SAME

(71) Applicant: Covidien LP, Mansfield, MA (US)

(72) Inventors: Jacob C. Baril, Norwalk, CT (US); Matthew A. Dinino, Newington, CT (US)

(73) Assignee: COVIDIEN LP, Mansfield, MA (US)

(*) Notice: Subject to any disclaimer, the term of this patent is extended or adjusted under 35 U.S.C. 154(b) by 232 days.

(21) Appl. No.: 16/120,598

(22) Filed: Sep. 4, 2018

(65) Prior Publication Data

US 2019/0133584 A1 May 9, 2019

Related U.S. Application Data

(60) Provisional application No. 62/581,144, filed on Nov. 3, 2017.

(51) Int. Cl.
*A61B 17/10* (2006.01)
*A61B 17/128* (2006.01)
(Continued)

(52) U.S. Cl.
CPC .......... *A61B 17/10* (2013.01); *A61B 17/1285* (2013.01); *A61B 2017/00367* (2013.01);
(Continued)

(58) Field of Classification Search
CPC .............. A61B 17/10; A61B 17/1285; A61B 2017/00389; A61B 2017/00464;
(Continued)

(56) References Cited

U.S. PATENT DOCUMENTS 3,120,230 A   2/1964   Skold
3,363,628 A   1/1968   Wood
(Continued)

FOREIGN PATENT DOCUMENTS

AU   2013254887 A1   11/2013
CA      1163889 A     3/1984
(Continued)

OTHER PUBLICATIONS

International Search Report corresponding to Int'l Patent Appln. PCT/US2018/050316 dated Dec. 31, 2018.
(Continued)

*Primary Examiner* — Ashley L Fishback

(57) ABSTRACT

A rotation knob assembly, handle assembly including the same, and surgical instrument including the same are disclosed. The rotation knob assembly includes an outer knob defining a lumen and at least one groove configured to receive an indexing protrusion of an elongated assembly to rotationally fix the elongated assembly relative to the outer knob. An inner collar is disposed within a proximal lumen portion of the outer knob and rotatably engaged therewith. A plurality of ball bearing assemblies protrude radially inwardly into the proximal lumen portion of the outer knob. Each ball bearing assembly includes a head and a ball bearing captured within the head. Each ball bearing is received within a waist of the inner collar such that, upon rotation of the outer knob relative to the inner collar, the ball bearings roll about a floor of the waist of the inner collar.

20 Claims, 6 Drawing Sheets

(51) Int. Cl.
*A61B 17/00* (2006.01)
*A61B 17/29* (2006.01)

(52) U.S. Cl.
CPC ............ *A61B 2017/00389* (2013.01); *A61B 2017/00407* (2013.01); *A61B 2017/00464* (2013.01); *A61B 2017/00469* (2013.01); *A61B 2017/00477* (2013.01); *A61B 2017/2922* (2013.01)

(58) Field of Classification Search
CPC .. A61B 2017/2922; A61B 2017/00367; A61B 2017/00407; A61B 2017/00469; A61B 2017/00477; B60K 37/06; G05G 1/08; G05G 1/10; G05G 1/12; H01H 3/08; H01H 3/10; H01H 19/14
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |

(56) References Cited

U.S. PATENT DOCUMENTS

| | | |
|---|---|---|
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,554,165 A * | 9/1996 | Raitt ............... B23D 51/10 30/340 |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |

(56) References Cited

U.S. PATENT DOCUMENTS

| | | |
|---|---|---|
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |

(56) References Cited

U.S. PATENT DOCUMENTS

| | | |
|---|---|---|
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |

(56) References Cited

U.S. PATENT DOCUMENTS

| | | |
|---|---|---|
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |

(56) References Cited

U.S. PATENT DOCUMENTS

| | | |
|---|---|---|
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |

(56) References Cited

U.S. PATENT DOCUMENTS

| | | |
|---|---|---|
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | | |
|---|---|---|---|
| CN | 103251441 A | | 8/2013 |
| CN | 104605911 B | | 2/2017 |
| CN | 107205747 A | | 9/2017 |
| DE | 202007003398 U1 | | 6/2007 |
| EP | 3132756 A1 | | 2/2017 |
| JP | 2011186812 A | | 9/2011 |
| JP | 2013166982 A | | 8/2013 |
| WO | 9003763 A1 | | 4/1990 |
| WO | 0042922 A1 | | 7/2000 |
| WO | 2016192096 A1 | | 12/2016 |
| WO | 2016192718 A2 | | 12/2016 |
| WO | 2016197350 A1 | | 12/2016 |
| WO | 2016206015 A1 | | 12/2016 |
| WO | 2017084000 A1 | | 5/2017 |
| WO | 2017146138 A1 | | 8/2017 |

OTHER PUBLICATIONS

International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

* cited by examiner

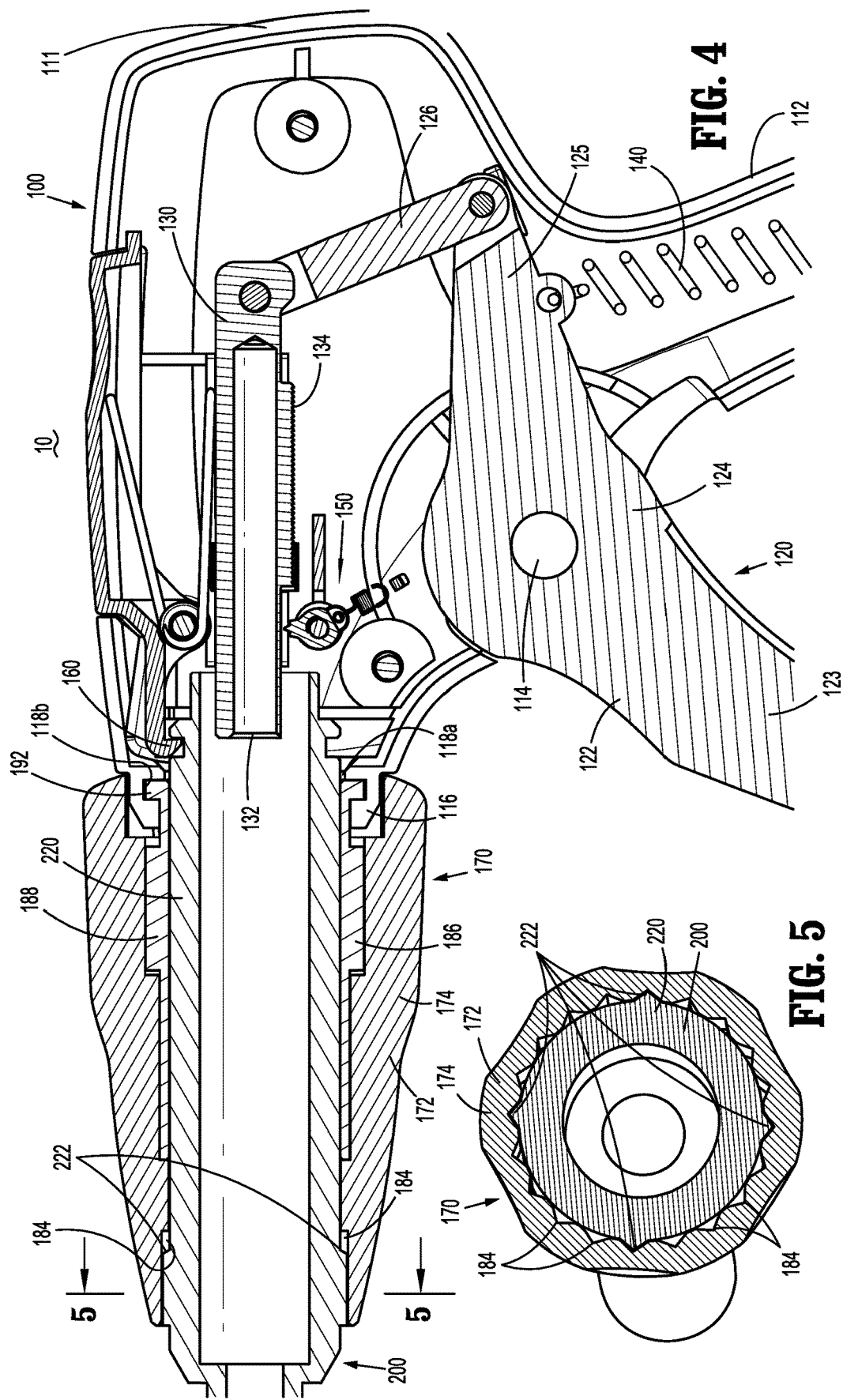

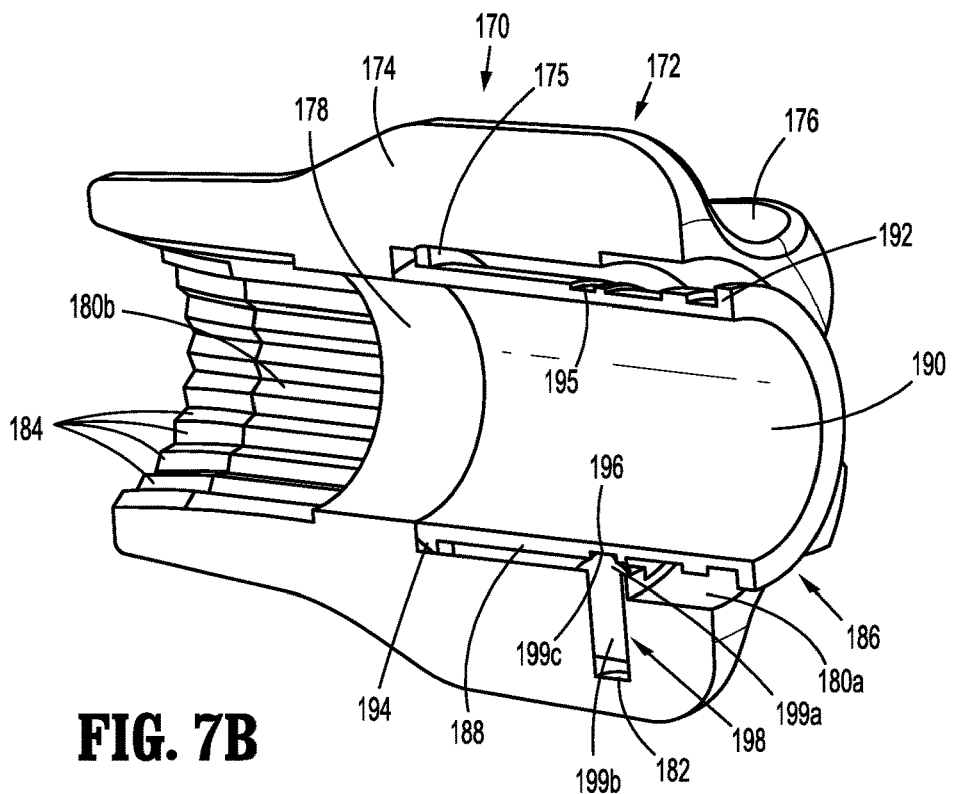
FIG. 7B
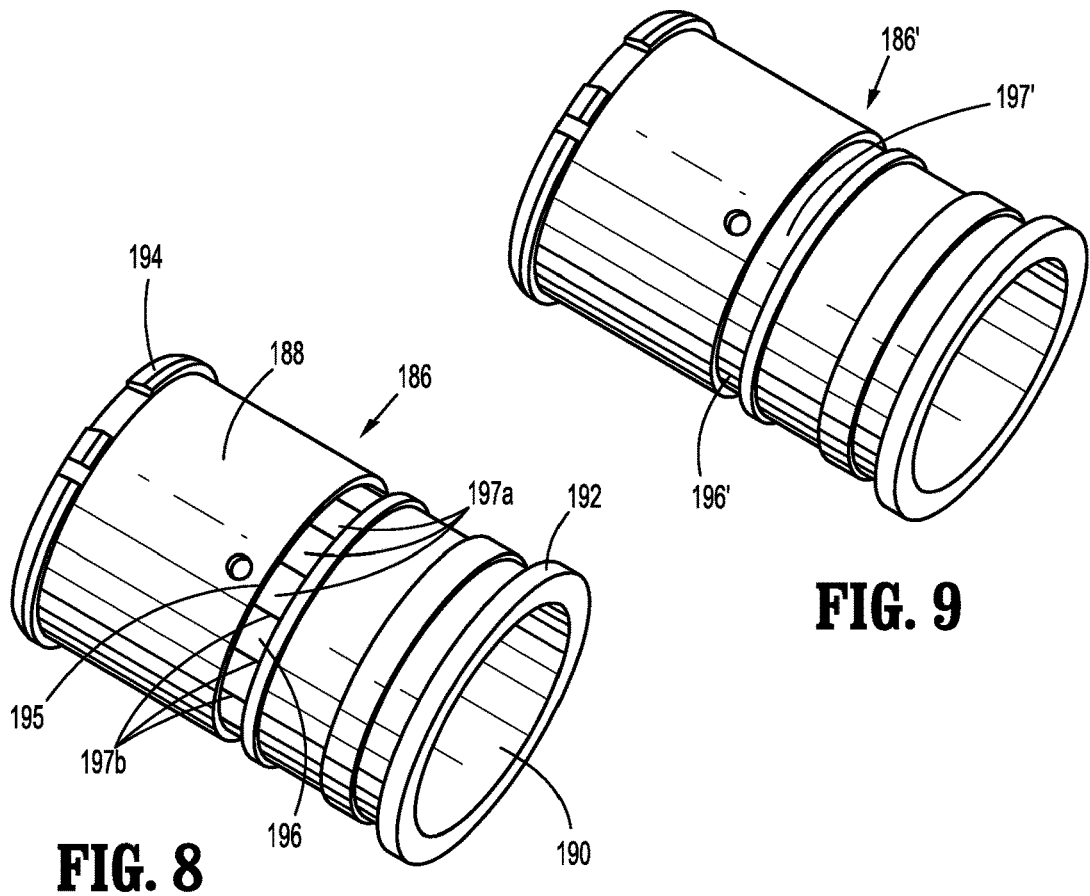
FIG. 8
FIG. 9

ROTATION KNOB ASSEMBLIES AND SURGICAL INSTRUMENTS INCLUDING THE SAME

CROSS-REFERENCE TO RELATED APPLICATION

This application claims the benefit of and priority to U.S. Provisional Patent Application No. 62/581,144 filed Jun. 28, 2018, the entire disclosure of which is incorporated by reference herein.

BACKGROUND

Technical Field

The present disclosure relates to surgical instruments such as, for example, surgical clip appliers. More particularly, the present disclosure relates to rotation knob assemblies for surgical clip appliers and surgical clip appliers including the same.

Description of Related Art

Surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures.

Endoscopic surgical clip appliers having various sizes (e.g., diameters), that are configured to apply a variety of diverse surgical clips, are also known in the art, and are capable of applying a single or multiple surgical clips during an entry to the body cavity. Such surgical clips are typically fabricated from a biocompatible material and are usually compressed over tissue. Once applied to tissue, the compressed surgical clip terminates the flow of fluid therethrough.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with aspects of the present disclosure is a rotation knob assembly for a surgical instrument. The rotation knob assembly includes an outer knob, an inner collar, and a plurality of ball bearing assemblies.

The outer knob includes a body defining a lumen extending longitudinally therethrough. The lumen includes a proximal lumen portion and a distal lumen portion. The body defines a plurality of grooves disposed on an interior surface thereof surrounding the distal lumen portion. One or more of the grooves is configured to receive a corresponding indexing protrusion of an elongated assembly inserted into the distal lumen portion to rotationally fix the elongated assembly relative to the outer knob.

The inner collar is disposed within the proximal lumen portion of the outer knob and rotatably engaged with the outer knob. The inner collar defines a waist including a floor recessed from an exterior annular surface of the inner collar.

Each of the ball bearing assemblies protrudes radially inwardly into the proximal lumen portion of the outer knob. Each ball bearing assembly includes a head and a ball bearing captured within the head. Each ball bearing is received within the waist of the inner collar such that, upon rotation of the outer knob relative to the inner collar, the ball bearings roll about the floor of the waist of the inner collar.

In an aspect of the present disclosure, the body of the outer knob defines a plurality of transverse apertures arranged annularly about and communicating with the proximal lumen portion. In such aspects, each ball bearing assembly includes a post extending from the head. Each post is received within one of the transverse apertures of the plurality of transverse apertures.

In another aspect of the present disclosure, the outer knob is formed from a polymeric material and the inner collar is formed from a metal.

In yet another aspect of the present disclosure, the floor of the waist defines a smooth surface such that the ball bearings are continuously rolled about the floor.

In still another aspect of the present disclosure, the floor of the waist includes a plurality of ramped segments angled relative to one another to define steps therebetween such that the ball bearings are rolled about the floor between a plurality of discrete positions. In such aspects, audible and/or tactile feedback may be provided as the ball bearings roll about the floor.

A handle assembly of a surgical instrument provided in accordance with aspects of the present disclosure includes a housing, a drive assembly, a trigger, and a rotation knob assembly. The housing defines a body portion, a fixed handle portion depending from the body portion, and a distal nose extending distally from the body portion. The drive assembly is disposed within the housing and the trigger is pivotably connected to the housing and operably associated with the drive assembly such that movement of the trigger relative to the fixed handle portion of the housing from an un-actuated position to an actuated position actuates the drive assembly. The rotation knob assembly extends distally from the distal nose of the housing and may include any of the features of the rotation knob assembly detailed above or otherwise herein. The inner collar of the rotation knob assembly is engaged with the distal nose of the housing in fixed rotational orientation relative to the housing.

In an aspect of the present disclosure, the distal nose of the housing defines an annular recess and the inner collar of the rotation knob assembly includes an annular protrusion configured for receipt within the annular recess to engage the inner collar with the distal nose.

In another aspect of the present disclosure, a latch assembly is operably associated with the housing. The latch assembly is configured to releasably engage an elongated assembly inserted through the rotation knob assembly and into the distal nose of the housing.

A surgical instrument provided in accordance with aspects of the present disclosure includes a handle assembly and an elongated assembly extending distally from the handle assembly. The elongated assembly supports an end effector assembly at a distal end portion thereof and includes an indexing protrusion disposed towards a proximal end portion thereof. The handle assembly of the surgical instrument may include any of the features detailed above or otherwise herein. The elongated assembly extends through the rotation knob assembly and the indexing protrusion thereof is received within the groove of the outer knob to rotationally fix the elongated assembly relative to the outer knob.

In an aspect of the present disclosure, the end effector of the elongated assembly is configured to fire and form at least one surgical clip about tissue in response to actuation of the drive assembly.

BRIEF DESCRIPTION OF THE DRAWINGS

Aspects and features of the presently-disclosed rotation knob assemblies for surgical clip appliers and surgical clip appliers including the same are described in detail with reference to the drawing figures wherein like reference numerals identify similar or identical structural elements and:

FIG. 4 is an enlarged, longitudinal, cross-sectional view of a portion of the handle assembly of the surgical clip applier of FIG. 1 including the elongated assembly of FIG. 1 engaged therewith;

FIG. 5 is an enlarged, transverse, cross-sectional view taken across section line "5-5" in FIG. 4;

FIG. 7B is a perspective, longitudinal, cross-sectional view of the rotation knob assembly of FIG. 6;

FIG. 8 is a perspective view of an inner collar of the rotation knob assembly of FIG. 6; and FIG. 9 is a perspective view of another inner collar configured for use with the rotation knob assembly of FIG. 6.

DETAILED DESCRIPTION

The present disclosure provides rotation knob assemblies for surgical instruments and surgical instruments including the same. Although detailed herein as incorporated into a surgical clip applier, the rotation knob assemblies of the present disclosure may alternatively be incorporated into any suitable surgical instrument.

Figure 1:
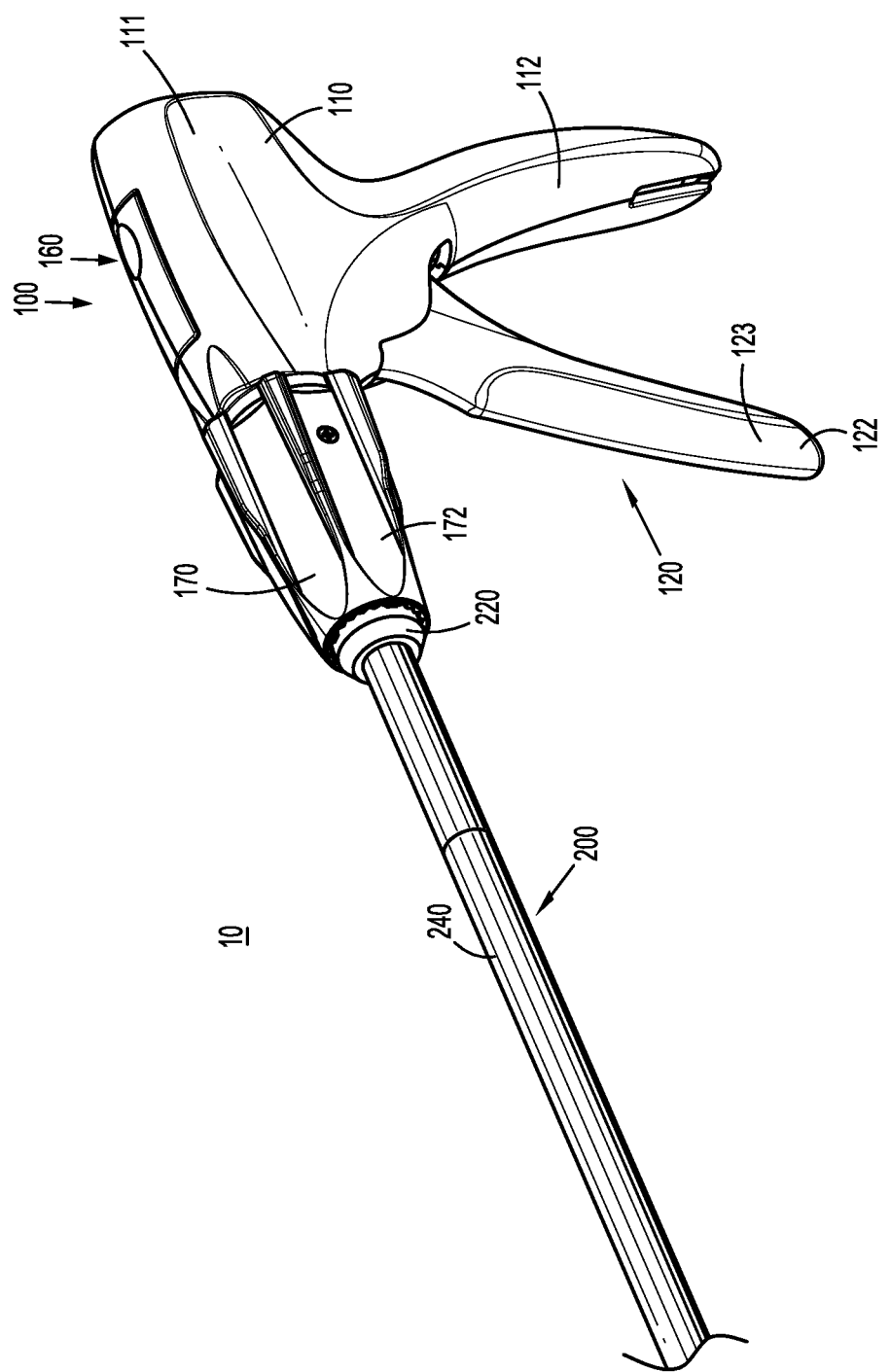
FIG. 1 is a front, perspective view of a surgical clip applier provided in accordance with the present disclosure including a handle assembly having an elongated assembly engaged therewith.
Figure 2:
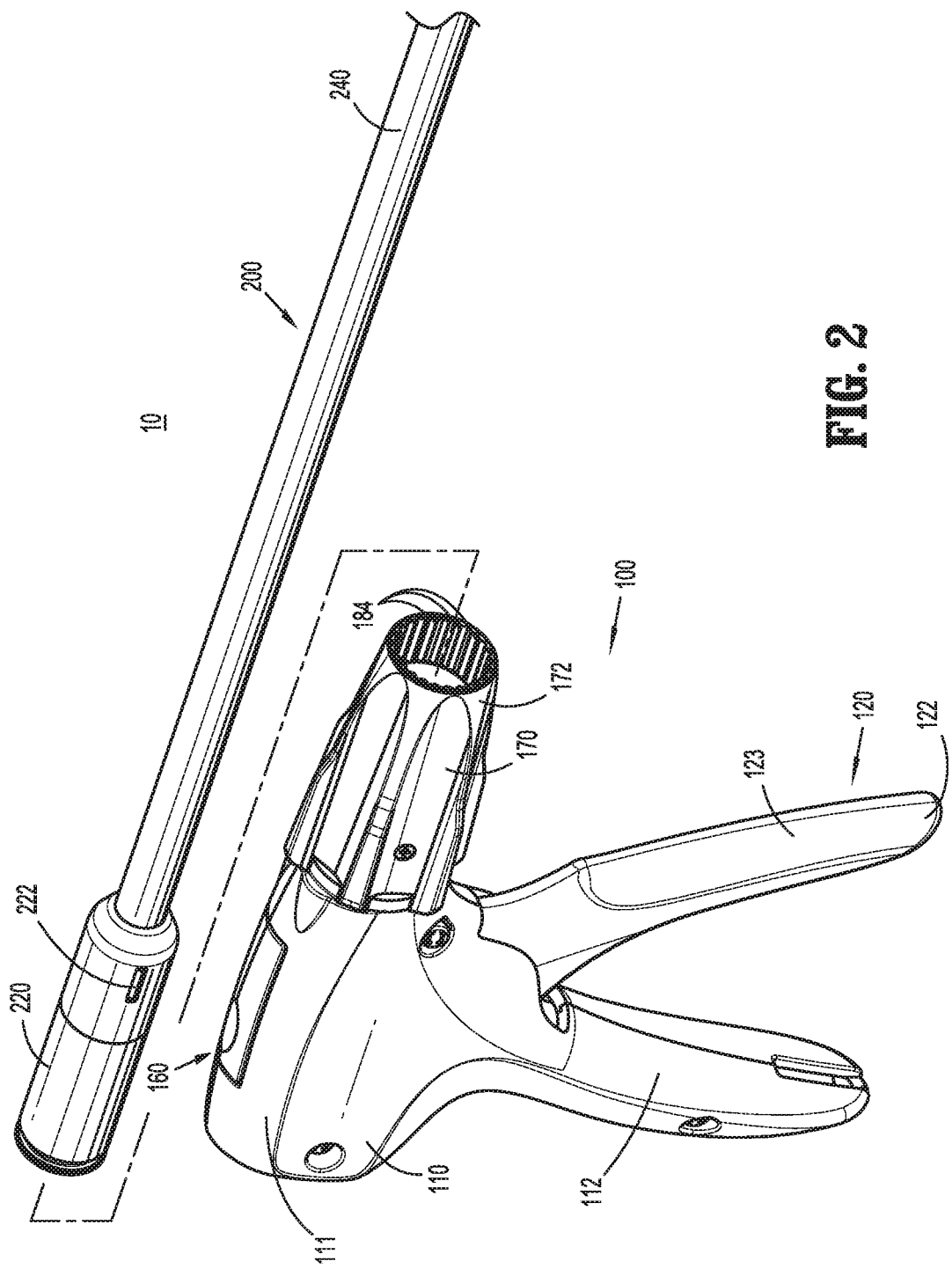
FIG. 2 is front, perspective view of the surgical clip applier of FIG. 1 with the elongated assembly removed from the handle assembly.

Turning to FIGS. 1-2, a surgical clip applier embodying the aspects and features of the present disclosure is shown generally identified by reference numeral 10. Surgical clip applier 10 generally includes a handle assembly 100 and a plurality of elongated assemblies 200, 300 (FIG. 3B) selectively connectable to handle assembly 100. Handle assembly 100 is configured to operate each of the plurality of elongated assemblies 200, 300 (FIG. 3B) upon connection thereto, and may be configured as a sterilizable, reusable component such that handle assembly 100 may be repeatedly used with different and/or additional elongated assemblies 200, 300 (FIG. 3B) during the course of one or more surgical procedures. The elongated assemblies 200, 300 (FIG. 3B) may be configured as single-use disposable components, limited-use disposable components, or reusable components, depending upon a particular purpose and/or the configuration of the particular elongated assembly. In either configuration, the need for multiple handle assemblies 100 is obviated and, instead, the surgeon need only select an appropriate elongated assembly 200, 300 (FIG. 3B) and connect that elongated assembly to handle assembly 100 in preparation for use.

Handle assembly 100 generally includes a housing 110, an actuation mechanism 120 operably associated with housing 110, a ratchet mechanism 150 (FIG. 4) operably disposed within housing 110, a latch assembly 160 operably associated with housing 110, and a rotation knob assembly 170 operably coupled to a distal portion of housing 110. Housing 110 supports and/or encloses the operating components of handle assembly 100 and is detailed below. Actuation mechanism 120, detailed below, is configured to enable selective firing of one or more surgical clips (not shown) from the end effector of the attached elongated assembly. Rotation knob assembly 170 enables the selective rotation of the attached elongated assembly relative to housing 110, and is also detailed below.

Ratchet mechanical 150 enables ratcheting advancement of drive bar 130 (FIG. 4) of actuation mechanism 120, when an elongated assembly configured for ratcheting actuation is connected to handle assembly 100. Latch assembly 160 is configured to facilitate releasable locking engagement of the elongated assembly with handle assembly 100. Details of a suitable ratchet mechanism 150 and/or latch assembly 160 can be found in International Application No. PCT/CN2016/096666, filed on Aug. 26, 2016, the entire contents of which is hereby incorporated herein by reference. Alternatively or additionally, ratchet mechanism 150 and/or latch assembly 160 may be configured as detailed in International Application No. PCT/CN2016/071178, filed on Jan. 18, 2016, the entire contents of which is also hereby incorporated herein by reference.

Figure 3A:
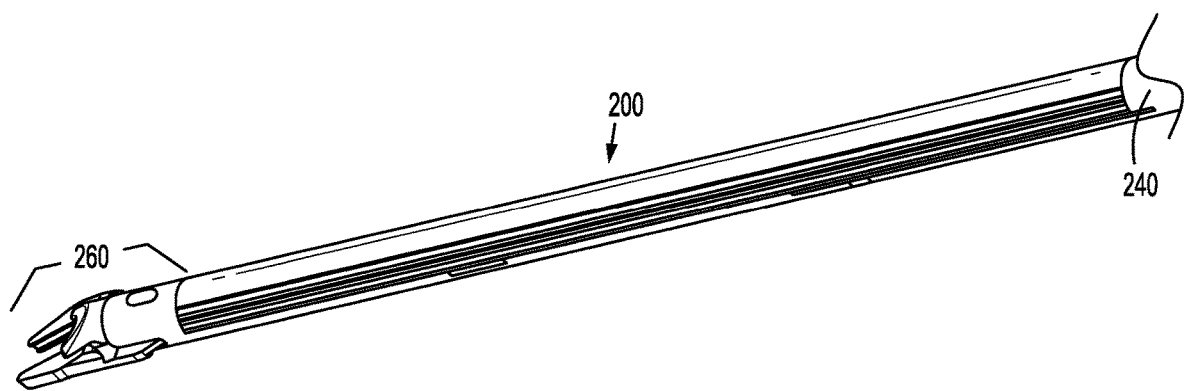
FIG. 3A is a side, perspective view of a distal end portion of the elongated assembly of FIGS. 1 and 2.
Figure 3B:
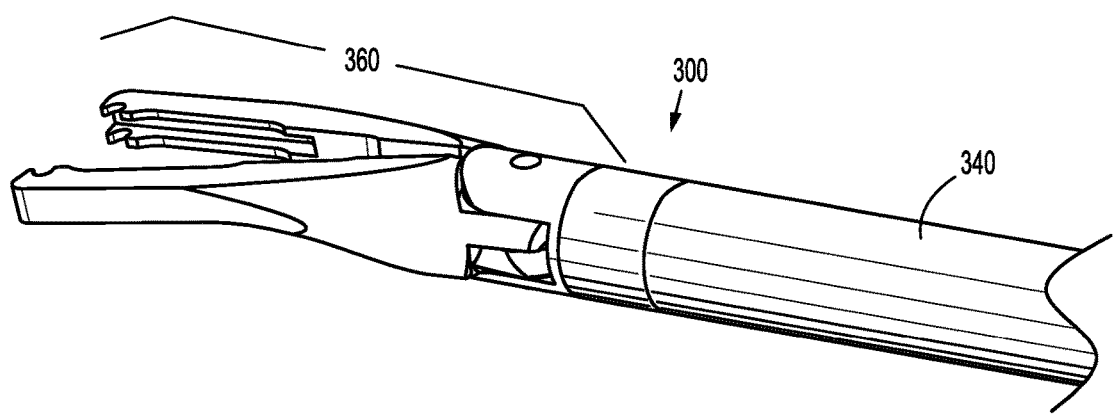
FIG. 3B is a side, perspective view of a distal end portion of another elongated assembly configured for use with the surgical clip applier of FIG. 1.
Figure 6:
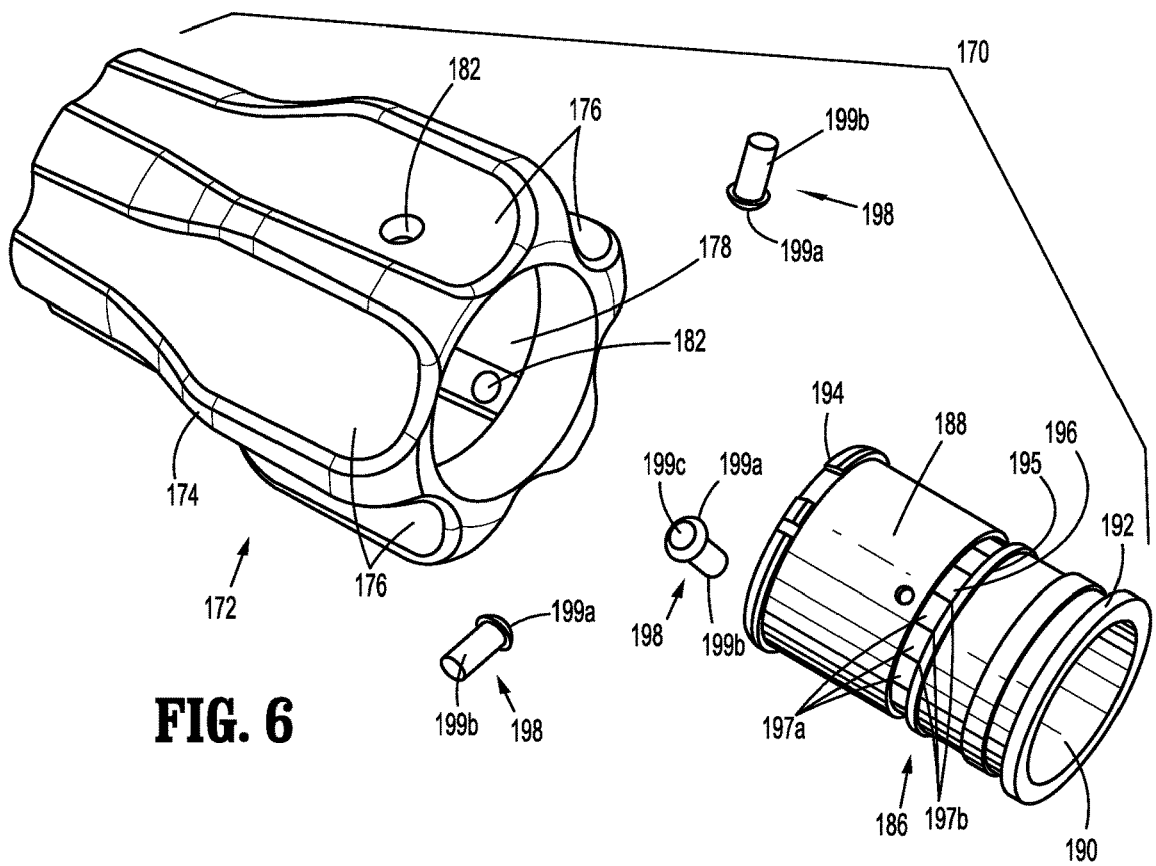
FIG. 6 is an exploded, perspective view of a rotation knob assembly of the handle assembly of the surgical clip applier of FIG. 1.
Figure 7A:
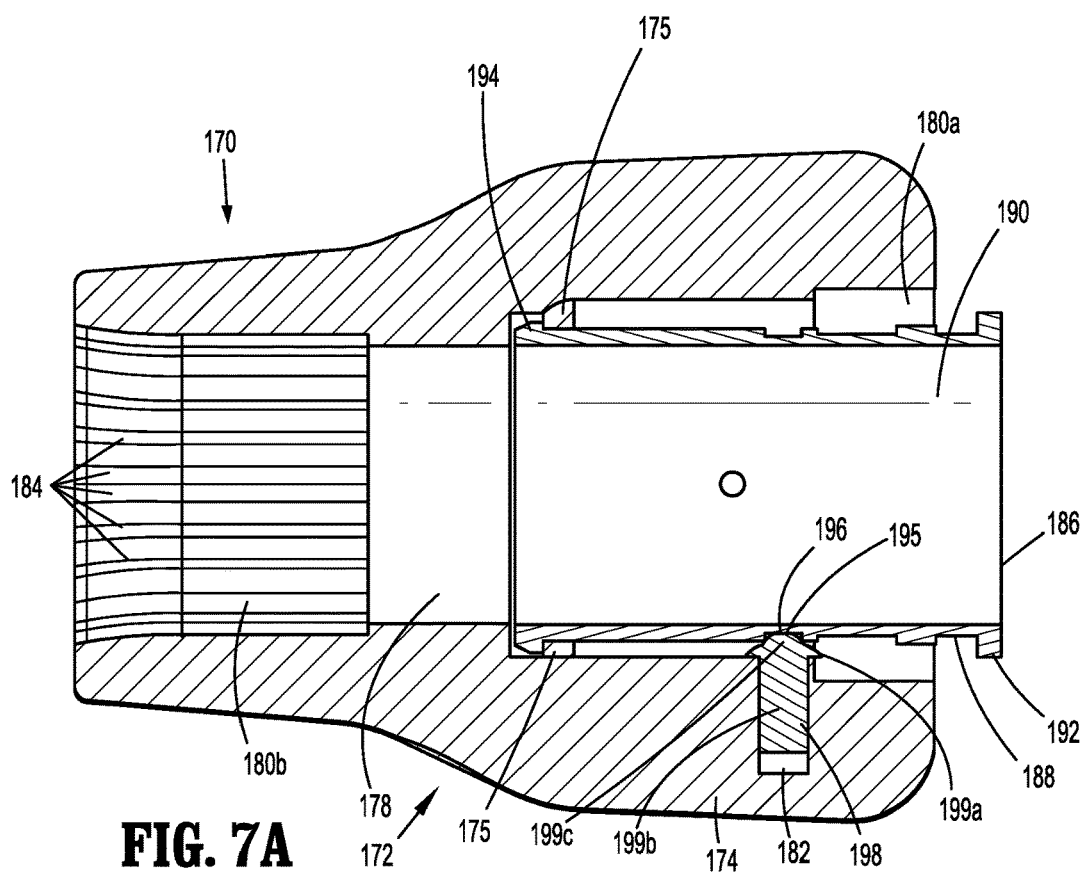
FIG. 7A is a side, longitudinal, cross-sectional view of the rotation knob assembly of FIG. 6.

With additional reference to FIGS. 3A and 3B, as noted above, handle assembly 100 is configured for use with different elongated assemblies such as, for example, elongated assembly 200 (FIGS. 1-3A) and elongated assembly 300 (FIG. 3B). Handle assembly 100, more specifically, is configured for both ratcheting use, e.g., in connection with elongated assembly 200 (FIGS. 1-3A), and non-ratcheting use, e.g., in connection with elongated assembly 300 (FIG. 3B). Elongated assemblies 200, 300 are described briefly below. A more detailed discussion of elongated assemblies, e.g., elongated assemblies 200, 300, configured for use with handle assembly 100 can be found in International Application Nos. PCT/CN2016/096666 and/or PCT/CN2016/071178, previously incorporated by reference herein in their entireties, and additionally or alternatively as in International Application No. PCT/CN2015/091603, filed on Oct. 10, 2015, the entire contents of which is likewise hereby incorporated herein by reference.

Referring to FIGS. 1-3A, elongated assembly 200 is configured for ratcheting use and generally includes a proximal hub 220, an elongated shaft 240 extending distally from proximal hub 220, an end effector assembly 260 disposed towards a distal end portion of elongated shaft 240, and an inner drive assembly (not shown) operably coupled between handle assembly 100 and end effector assembly 260 when elongated assembly 200 is engaged with handle assembly 100 to enable the sequential firing of at least one surgical clip (not shown) about tissue. End effector assembly 260 of elongated assembly 200 may be configured to fire surgical clips similar to those shown and described in U.S. Pat. No. 7,819,886 or 7,905,890, the entire contents of each of which is hereby incorporated herein by reference.

Proximal hub 220 of elongated assembly 200 defines a plurality of indexing protrusions 222 annularly disposed thereabout towards a distal end portion thereof. Indexing protrusions 222, as detailed below, are configured for slidable receipt within longitudinally-extending grooves 184 defined within outer knob 172 of rotation knob assembly 170 to rotationally fix proximal hub 220 of elongated assembly 200 relative to rotation knob assembly 170 upon insertion of proximal hub 220 therethrough (see also FIG. 5). As such, in use, rotation of outer knob 172 of rotation knob assembly 170 relative to housing 110 effects corresponding rotation of elongated assembly 200 relative to housing 110.

Referring to FIG. 3B, in conjunction with FIGS. 1 and 2, elongated assembly 300 is configured for non-ratcheting use and generally includes a proximal hub (not shown), an elongated shaft 340 extending distally from the proximal hub, an end effector assembly 360 disposed towards a distal end portion of elongated shaft 340, and an inner drive assembly (not shown) operably coupled between handle assembly 100 and end effector assembly 360 when elongated assembly 300 is engaged with handle assembly 100 to enable grasping and/or manipulation of tissue, retrieval of a surgical clip, and firing of the surgical clip about tissue. It is contemplated that end effector assembly 360 of elongated assembly 300 may be configured to fire surgical clips similar to those shown and described in U.S. Pat. No. 4,834,096, the entire contents of which is hereby incorporated herein by reference.

The proximal hub (not shown) of elongated assembly 300 includes indexing protrusions similarly as detailed above with respect to proxy hub 220 of elongated assembly 200 (see FIG. 2) such that elongated assembly 300 is rotationally fix relative to rotation knob assembly 170 upon insertion of proximal hub 220 therethrough to enable rotation of elongated assembly 300 relative to housing 110 in response to rotation of outer knob 172 of rotation knob assembly 170 relative to housing 110.

Referring generally to FIGS. 1-3B, although exemplary elongated assemblies 200, 300 configured for ratcheting and non-ratcheting use, respectively, are detailed above, it is contemplated that various other elongated assemblies for performing various different surgical tasks and/or having various different configurations suitable for ratcheting or non-ratcheting use may likewise be utilized with handle assembly 100.

Turning to FIGS. 1, 2, and 4, housing 110 of handle assembly 100 may be formed from first and second housing halves that cooperate to define a body portion 111 and a fixed handle portion 112 depending from body portion 111. Body portion 111 of housing 110 includes an internal pivot post 114 extending transversely within body portion 111, and a distal nose 116 defining a distal opening 118 therethrough. A proximal end portion of a proximal hub of an elongated assembly, e.g., proximal hub 220 of elongated assembly 200 (FIGS. 1-3A) or the proximal hub (not shown) of elongated assembly 300 (FIG. 3B), is configured to extend at least partially through distal opening 118a of distal nose 116 of housing 110 when the elongated assembly 200 or 300 is engaged with handle assembly 100 (see FIG. 4). Distal nose 116 of body portion 111 of housing 110 further includes an annular recess 118b defined on an interior surface thereof surrounding distal opening 118a. Annular recess 118b is configured to receive annular protrusion 192 of inner collar 186 of rotation knob assembly 170 to fixedly engage rotation knob assembly 170 with distal nose 116 of body portion 111 of housing 110. To this end, annular recess 118b and/or annular protrusion 192 of inner collar 186 may include keying features or other suitable features or materials (not shown) to facilitate rotationally-locked engagement between inner collar 186 and distal nose 116 of housing 110.

Actuation mechanism 120 is operably supported by housing 110 and includes a trigger 122, a linkage 126, a drive bar 130, and a biasing member 140. Trigger 122 includes a grasping portion 123, an intermediate pivot portion 124, and a proximal extension 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture configured to receive pivot post 114 of housing 110 so as to enable pivoting of trigger 122 about pivot post 114 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension 125 of trigger 122 is disposed on an opposite side of intermediate pivot portion 124 and, thus, pivot post 114, as compared to grasping portion 123 of trigger 122. As such, pivoting of grasping portion 123 to rotate in one direction, e.g., proximally towards fixed handle portion 112, pivots proximal extension 125 to rotate in the opposite direction, e.g., distally. Proximal extension 125 of trigger 122 is pivotably coupled to the proximal end of linkage 126. Biasing member 140 is secured at either end and extends between proximal extension portion 125 of trigger 122 and a support (not shown) disposed within fixed handle portion 112 of housing 110. Pivoting of grasping portion 123 towards the actuated position elongates biasing member 140 storing energy therein such that, upon release of grasping portion 123, grasping portion 123 is returned towards the un-actuated position under the bias of biasing member 140. Although illustrated as an extension coil spring, biasing member 140 may define any suitable configuration for biasing grasping portion 123 of trigger 122 towards the un-actuated position.

As noted above, linkage 126 is coupled at its proximal end to proximal extension portion 125 of trigger 122. Linkage 126 is also pivotably coupled at its distal end to a proximal end of drive bar 130. As a result of this configuration, pivoting of grasping portion 123 of trigger 122 towards the actuated position urges proximal extension portion 125 of trigger 122 distally which, in turn, urges linkage 126 distally to, in turn, urge drive bar 130 distally.

Drive bar 130 is slidable through body portion 111 of housing 110, in response to actuation of trigger 122, to urge a distal end portion 132 of drive bar 130 into contact with a proximal actuator of an inner drive assembly (not shown) of an elongated assembly, e.g., elongated assembly 200 (FIGS. 1-3A) or elongated assembly 300 (FIG. 3B), engaged with handle assembly 100 to fire a surgical clip supported at the end effector assembly of the elongated assembly. Drive bar 130, more specifically, is slidable from an un-actuated, proximal position, corresponding to the un-actuated position of grasping portion 123 of trigger 122, to an actuated, distal position, corresponding to the actuated position of grasping portion 123 of trigger 122, in order to urge the proximal actuator of the inner drive assembly (not shown) of the elongated assembly distally to fire a surgical clip supported at the end effector assembly of the elongated assembly.

Drive bar 130 may further include a ratchet rack 134 extending along at least a portion of an underside surface thereof. Ratchet rack 134 is configured to selectively interface with ratchet mechanism 150 to enable advancement of drive bar 130 in either a ratcheting condition or a non-ratcheting condition. Ratchet rack 134 and ratchet mechanism 150, as noted above, may be configured similarly as described in, for example, International Application No. PCT/CN2016/096666 or International Application No. PCT/CN2016/071178, each of which was previously incorporated by reference herein.

With reference to FIGS. 4-8, as noted above, rotation knob assembly 170 is rotatably coupled to distal nose 116 of body portion 111 of housing 110 and is configured to receive the proximal hub of the elongated assembly, e.g., proximal hub 220 of elongated assembly 200, coupled to handle assembly 100 in fixed rotational engagement therewith to enable selective rotation of elongated assembly 200 relative to housing 110 upon rotation of outer knob 172 of rotation knob assembly 170 relative to housing 110. Rotation knob assembly 170 includes outer knob 172, an inner collar 186, and a plurality, e.g., three, ball bearing assemblies 198.

Referring to FIGS. 4-7B, outer knob 172 of rotation knob assembly 170 may be formed from a polymeric material, e.g., a biocompatible, sterilizable plastic, or other suitable material, and includes a body 174 defining a cone shaped-configuration tapering in diameter from a proximal end portion to a distal end portion thereof, although other suitable configurations are also contemplated. Body 174 defines a plurality of flutes 176 arranged radially about body 174 to facilitate grasping or gripping body 174 at any rotational orientation to enable rotation thereof.

Body 174 of outer knob 172 of rotation knob assembly 170 further includes a longitudinally-extending lumen 178 defined therethrough. Longitudinally-extending lumen 178 includes a proximal portion 180a and a distal portion 180b, which may define equal or different diameters, e.g., proximal portion 180a may define a larger diameter as compared to distal portion 180b. Proximal portion 180a of lumen 178 communicates with the proximal opening of body 174 of outer knob 172. A plurality, e.g., three, transverse apertures 182 equally-spaced annularly about body 174 of outer knob 172 are defined through body 174 of outer knob 172 and communicate with proximal portion 180a of lumen 178. Each transverse aperture 182 is configured to receive one of the ball bearing assemblies 198 as detailed below.

Distal portion 180b of lumen 178 communicates with the distal opening of body 174 of outer knob 172 at the distal end thereof and with proximal portion 180a of lumen 178 at the proximal end thereof. Body 174 includes a plurality of longitudinally-extending grooves 184 arranged annularly on an interior surface thereof and disposed about at least a portion of distal portion 180b of lumen 178. As noted above, grooves 184 are configured to slidably receive indexing protrusions 222 of proximal hub 220 of elongated assembly 200 (see FIGS. 2 and 5) to rotationally fix proximal hub 220 relative to outer knob 172 upon insertion of proximal hub 220 into handle assembly 100.

Inner collar 186 of rotation knob assembly 180 may be formed from a metal, e.g., stainless steel, or other suitable material, and includes a body 188 defining a longitudinally-extending lumen 190 therethrough. Inner collar 186 further includes an annular protrusion 192 disposed about the proximal end portion thereof, a distal head 194 disposed about the distal end portion thereof, and a waist or channel 195 defined annularly within an exterior surface of inner collar 186 and disposed between annular protrusion 192 and distal head 194. Annular protrusion 192, as noted above, is configured for receipt within annular recess 118b of distal nose 116 of housing 110 (see FIG. 4) to fixedly engage inner collar 186 with distal nose 116 of body portion 111 of housing 110, e.g., upon engagement of the housing halves forming housing 110 with one another.

Inner collar 186 is configured to accept body 174 of outer knob 172 thereabout such that inner collar 186 is received within proximal portion 180a of lumen 178 of body 174 of outer knob 172 through the proximal opening thereof. Distal head 194 of inner collar 186 defines a chamfered distally-facing edge such that, upon receipt of inner collar 186 within proximal portion 188a of lumen 178, distal head 194 is cammed over an internal annular rib 175 disposed on an internal surface of body 174 of outer knob 172 about proximal portion 180a of lumen 178 to longitudinally fix inner collar 186 within outer knob 172 while still permitting relative rotation therebetween. Distal head 194 may be sectioned, e.g., distal head 194 need not extend about the full annular periphery of inner collar 186, to facilitate the above-detailed engagement of inner collar 186 within outer knob 172.

Waist 195 of inner collar 186 includes a recessed floor 196 that is recessed relative to the exterior surface of inner collar 186. Upon rotatable engagement of outer knob 172 about inner collar 186, as detailed above, recessed floor 196 of waist 195 is aligned with each of transverse apertures 182 defined within outer knob 172.

With reference to FIG. 8, in embodiments, recessed floor 196 may include a plurality of ramped segments 197a (or an annular array of concavities/recesses) angled relative to one another to define steps 197b therebetween, thus defining a ratchet-like configuration. Alternatively, in other embodiments, with reference to FIG. 9, an inner collar 186' may be provided whereby recessed floor 196' defines a smooth surface 197'. Inner collar 186' may otherwise be similar to inner collar 186 (FIG. 8).

Referring again to FIGS. 6-7B, each ball bearing assembly 198 (e.g., spring ball bearing assembly) includes a head 199a, a post 199b extending from the respective head 199a thereof, and a ball bearing 199c captured within the respective head 199a thereof such that a portion of the ball bearing 199c protrudes from the head 199a and is rotatable relative thereto. Posts 199b of ball bearing assemblies 198 are configured for receipt within transverse apertures 182 defined through body 174 of outer knob 172, with ball bearing assemblies 198 oriented such that heads 199a and ball bearings 199c protrude radially inwardly into proximal portion 180a of lumen 178 of body 174 of outer knob 172. Ball bearing assemblies 198 may each further include a biasing member (not shown) disposed therein and configured to bias ball bearings 199c to protrude outwardly from heads 199a.

As noted above, upon rotatable engagement of outer knob 172 about inner collar 186, as detailed above, recessed floor 196 of waist 195 of inner collar 186 is aligned with each of transverse apertures 182 defined within outer knob 172. More specifically, since ball bearing assemblies 198 are engaged within transverse apertures 182, upon rotatable engagement of outer knob 172 about inner collar 186 (with ball bearing assemblies 198 already installed), ball bearings 199c protrude into waist 195 into abutment with recessed floor 196. The receipt of ball bearings 199c within waist 195 guides rotation of outer knob 172 relative to inner collar 186, enabling ball bearings 199c to roll about recessed floor 196 with minimal friction, thus providing ease of rotation for the user.

In embodiments where recessed floor 196 defines a ratchet-like or stepped configuration (FIGS. 6 and 8), outer knob 172 is rotatable about inner collar 186 in a plurality of discrete increments, with each discrete position corresponding to positioning of ball bearings 199c adjacent steps 197b of recessed floor 196. The particular increment depends upon the lengths of ramped segments 197a of recessed floor 196. Further, audible and/or tactile feedback, in the form of a "click" may be provided in such embodiments. On the other hand, in embodiments where inner collar 186' is provided with a smooth surface 197' (see FIG. 9), outer knob 172 may be rotated continuously through an infinite number of positions.

Referring generally to FIGS. 1, 2, 4, and 6, insertion and engagement of an elongated assembly, e.g., elongated assembly 200, with handle assembly 100 and use of the same are described.

In order to engage elongated assembly 200 with handle assembly 100, proximal hub 220 of elongated assembly 200 is inserted through the distal opening of outer knob 172 of rotation knob assembly 170, distal portion 180b of lumen 178 of outer knob 172, lumen 190 of inner collar 186 of rotation knob assembly 170, and into distal nose 116 of housing 110, wherein latch assembly 160 cams over the proximal end of proximal hub 220 and into engagement therewith to thereby rotatably engage proximal hub 220 relative to housing 110 and, thus, relative to inner collar 186. Upon insertion of proximal hub 220 through rotation knob assembly 170, as noted above, indexing protrusions 222 of proximal hub 220 are received within longitudinally-extending grooves 184 of outer knob 172 to rotationally fix proximal hub 220 relative to outer knob 172 (see FIG. 5).

With elongated assembly 200 engaged with handle assembly 100 as detailed above, handle assembly 100 may be manipulated and/or outer knob 172 rotated to position end effector 260 (FIG. 3A) of elongated assembly 200 about tissue to be treated. Once end effector 260 is positioned as desired, trigger 122 is pivoted towards fixed handle portion 112 of housing 110 to urge linkage 126 distally which, in turn, urges drive bar 130 distally through housing 110 to drive the proximal actuator of the inner drive assembly (not shown) of elongated assembly 200 distally through elongated assembly 200 to fire and form a surgical clip from end effector assembly 260 (FIG. 3A) about tissue. The above may be repeated to fire and form several surgical clips about tissue, as necessary.

In order to disengage elongated assembly 200 from handle assembly 100, e.g., for cleaning and/or sterilization, or to replace elongated assembly 200 with another endoscopic assembly, latch assembly 160 is depressed inwardly into housing 110 to disengage proximal hub 220 of elongated assembly 200, thus enabling proximal hub 220 to be withdrawn distally from housing 110 and rotation knob assembly 170.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A rotation knob assembly for a surgical instrument, the rotation knob assembly comprising:
    an outer knob including a body defining a lumen extending longitudinally therethrough, the lumen including a proximal lumen portion and a distal lumen portion, the body defining a plurality of grooves disposed on an interior surface thereof surrounding the distal lumen portion, at least one groove of the plurality of grooves configured to receive a corresponding indexing protrusion of an elongated assembly inserted into the distal lumen portion to rotationally fix the elongated assembly relative to the outer knob;
    an inner collar disposed within the proximal lumen portion of the outer knob and rotatably engaged with the outer knob, the inner collar defining a waist including a floor recessed from an exterior annular surface of the inner collar; and
    a plurality of ball bearing assemblies protruding radially inwardly into the proximal lumen portion of the outer knob, each ball bearing assembly of the plurality of ball bearing assemblies including a head and a ball bearing captured within the head, each ball bearing received within the waist of the inner collar such that, upon rotation of the outer knob relative to the inner collar, the ball bearings roll about the floor of the waist of the inner collar.

2. The rotation knob assembly according to claim 1, wherein:
    the body of the outer knob defines a plurality of transverse apertures arranged annularly about and communicating with the proximal lumen portion, and
    each ball bearing assembly of the plurality of ball bearing assemblies includes a post extending from the head, each post received within one of the transverse apertures of the plurality of transverse apertures.

3. The rotation knob assembly according to claim 1, wherein the outer knob is formed from a polymeric material and the inner collar is formed from a metal.

4. The rotation knob assembly according to claim 1, wherein the floor of the waist defines a smooth surface such that the ball bearings are continuously rolled about the floor.

5. The rotation knob assembly according to claim 1, wherein the floor of the waist includes a plurality of ramped segments angled relative to one another to define steps therebetween such that the ball bearings are rolled about the floor between a plurality of discrete positions.

6. The rotation knob assembly according to claim 5, wherein at least one of audible or tactile feedback is provided as the ball bearings roll about the floor.

7. A handle assembly of a surgical instrument, comprising:
    a housing defining a body portion, a fixed handle portion depending from the body portion, and a distal nose extending distally from the body portion;
    a drive assembly disposed within the housing;
    a trigger pivotably connected to the housing and operably associated with the drive assembly, the trigger movable relative to the fixed handle portion of the housing from an un-actuated position to an actuated position to actuate the drive assembly; and
    a rotation knob assembly extending distally from the distal nose of the housing, the rotation knob assembly including:

an outer knob including a body defining a lumen extending longitudinally therethrough, the lumen including a proximal lumen portion and a distal lumen portion, the body defining a plurality of grooves disposed on an interior surface thereof surrounding the distal lumen portion, at least one groove of the plurality of grooves configured to receive a corresponding indexing protrusion of an elongated assembly inserted through the rotation knob assembly and into the distal nose of the housing to rotationally fix the elongated assembly relative to the outer knob;

an inner collar engaged with the distal nose of the housing in fixed rotational orientation relative to the housing, the inner collar disposed within the proximal lumen portion of the outer knob and rotatably engaged with the outer knob, the inner collar defining a waist including a floor recessed from an exterior annular surface of the inner collar; and a plurality of ball bearing assemblies protruding radially inwardly into the proximal lumen portion of the outer knob, each ball bearing assembly of the plurality of ball bearing assemblies including a head and a ball bearing captured within the head, each ball bearing received within the waist of the inner collar such that, upon rotation of the outer knob relative to the inner collar and the housing, the ball bearings roll about the floor of the waist of the inner collar.

8. The handle assembly according to claim 7, wherein:
the body of the outer knob defines a plurality of transverse apertures arranged annularly about and communicating with the proximal lumen portion, and
each ball bearing assembly of the plurality of ball bearing assemblies includes a post extending from the head, each post received within one of the transverse apertures of the plurality of transverse apertures.

9. The handle assembly according to claim 7, wherein the outer knob is formed from a polymeric material and the inner collar is formed from a metal.

10. The handle assembly according to claim 7, wherein the floor of the waist defines a smooth surface such that the ball bearings are continuously rolled about the floor.

11. The handle assembly according to claim 7, wherein the floor of the waist includes a plurality of ramped segments angled relative to one another to define steps therebetween such that the ball bearings are rolled about the floor between a plurality of discrete positions.

12. The handle assembly according to claim 11, wherein at least one of audible or tactile feedback is provided as the ball bearings roll about the floor.

13. The handle assembly according to claim 7, wherein the distal nose of the housing defines an annular recess and wherein the inner collar includes an annular protrusion configured for receipt within the annular recess to engage the inner collar with the distal nose.

14. The handle assembly according to claim 7, further comprising a latch assembly operably associated with the housing, wherein the latch assembly is configured to releasably engage an elongated assembly inserted through the rotation knob assembly and into the distal nose of the housing.

15. A surgical instrument, comprising:
a handle assembly; and
an elongated assembly extending distally from the handle assembly and supporting an end effector assembly at a distal end portion thereof, the elongated assembly including an indexing protrusion disposed towards a proximal end portion thereof;
wherein the handle assembly includes:
a housing defining a body portion, a fixed handle portion depending from the body portion, and a distal nose extending distally from the body portion;
a drive assembly disposed within the housing;
a trigger pivotably connected to the housing and operably associated with the drive assembly, the trigger movable relative to the fixed handle portion of the housing from an un-actuated position to an actuated position to actuate the drive assembly; and
a rotation knob assembly extending distally from the distal nose of the housing and disposed about the elongated assembly, the rotation knob assembly including:
an outer knob including a body defining a lumen extending longitudinally therethrough, the lumen including a proximal lumen portion and a distal lumen portion, the body defining a plurality of grooves disposed on an interior surface thereof surrounding the distal lumen portion, one groove of the plurality of grooves configured to receive the indexing protrusion of the elongated assembly to rotationally fix the elongated assembly relative to the outer knob;
an inner collar engaged with the distal nose of the housing in fixed rotational orientation relative to the housing, the inner collar disposed within the proximal lumen portion of the outer knob and rotatably engaged with the outer knob, the inner collar defining a waist including a floor recessed from an exterior annular surface of the inner collar; and
a plurality of ball bearing assemblies protruding radially inwardly into the proximal lumen portion of the outer knob, each ball bearing assembly of the plurality of ball bearing assemblies including a head and a ball bearing captured within the head, each ball bearing received within the waist of the inner collar such that, upon rotation of the outer knob relative to the inner collar and the housing, the ball bearings roll about the floor of the waist of the inner collar.

16. The surgical instrument according to claim 15, wherein:
the body of the outer knob defines a plurality of transverse apertures arranged annularly about and communicating with the proximal lumen portion, and
each ball bearing assembly of the plurality of ball bearing assemblies includes a post extending from the head, each post received within one of the transverse apertures of the plurality of transverse apertures.

17. The surgical instrument according to claim 15, wherein the floor of the waist defines a smooth surface such that the ball bearings are continuously rolled about the floor.

18. The surgical instrument according to claim 15, wherein the floor of the waist includes a plurality of ramped segments angled relative to one another to define steps therebetween such that the ball bearings are rolled about the floor between a plurality of discrete positions.

19. The surgical instrument according to claim 15, further comprising a latch assembly operably associated with the housing, wherein the latch assembly is configured to releasably engage the elongated assembly with the housing.

20. The surgical instrument according to claim 15, wherein the end effector is configured to fire and form at least one surgical clip about tissue in response to actuation of the drive assembly.

* * * * *